United States Patent [19]

Kohl

[11] Patent Number: 5,233,982

[45] Date of Patent: Aug. 10, 1993

[54] METHOD AND APPARATUS FOR DEFINING A PARAMETER DURING THE OUTPUT OF AN ELECTRICAL PULSE TO BIOLOGICAL TISSUE

[75] Inventor: Martin Kohl, Braeuningshof, Fed. Rep. of Germany

[73] Assignee: Siemens Aktiengesellschaft, Munich

[21] Appl. No.: 790,505

[22] Filed: Nov. 12, 1991

[30] Foreign Application Priority Data

Nov. 29, 1990 [EP] European Pat. Off. ........ 90122888.2

[51] Int. Cl.$^5$ ............................................. A61N 5/01
[52] U.S. Cl. ...................................... 607/5; 128/734; 607/65
[58] Field of Search ................. 128/419 D, 734; 324/649, 650, 677, 678

[56] References Cited

FOREIGN PATENT DOCUMENTS 0315368 5/1989 European Pat. Off. .
2085593 4/1982 United Kingdom .

OTHER PUBLICATIONS

"A Reliable Microprocessor-Based Defibrillator Analyzer," Sharma et al. IEEE Trans. Instr. and Meas., vol. IM-31, No. 1, Mar., 1982 pp. 28-31.

"Thoracic Impedance of Human Subject," Machin, Medical & Biological Eng. & Comp., vol. 16, No. 2 (1978) pp. 169-178.

"Stimulators, Defibrillator," Medical Electronics, pp. 156-158 (Oct. 9, 1990).

Primary Examiner—Lee S. Cohen
Assistant Examiner—Jeffrey R. Jastrzab
Attorney, Agent, or Firm—Hill, Steadman & Simpson

[57] ABSTRACT

A method and apparatus for defining at least one variable parameter of an electrical pulse supplied from an RLC discharge circuit as an output to biological tissue, independently of the amplitude of the pulse, are disclosed wherein a measurement of the chronological spacing between two values of the pulse at different times is undertaken, and the chronological spacing is evaluated, with the result of the evaluation being used to define a parameter of the RLC discharge circuit.

27 Claims, 2 Drawing Sheets

METHOD AND APPARATUS FOR DEFINING A PARAMETER DURING THE OUTPUT OF AN ELECTRICAL PULSE TO BIOLOGICAL TISSUE

BACKGROUND OF THE INVENTION

1. Field of the Invention

The present invention is directed to a method for defining at least one parameter in a RLC discharge circuit during the output of an electrical pulse to biological tissue, and to an apparatus for the implementation of the method, of the type having a storage capacitor and a coil which can be connected via biological tissue to form an RLC discharge circuit to which a measuring means having an evaluation circuit is coupled.

2. Description of the Prior Art

A method and an apparatus of this type are known from the periodical Medical Electronics, October 1986, pages 156-158 and are set forth therein in combination with a defibrillator. For medical as well as legal reasons, a measurement and subsequent documentation of the critical parameters present upon the output of an electrical pulse for defibrillation in the discharge circuit are required. The resistance of the biological tissue, for example, the patient resistance, the energy stored in the charging capacitor (storage capacitor), as well as the energy that results from these two parameters and is supplied to the patient (living biological tissue) are all commonly used as variable parameters. In the above known apparatus, a measuring means is connected via a current transformer to an RLC discharge circuit for the definition of such parameters. The discharge current (the output electrical pulse) flows through the primary side of the current transformer. The secondary side of the transformer is loaded with a load resistor and is connected to the measuring means. The measuring means is fashioned such that the maximum value of the secondary voltage of the transformer is measured and is evaluated in a microprocessor for identifying the patient resistance.

Consequently, the precision of this measuring method is dependent on the magnitude of the amplitude of the secondary voltage of the induced current. Leaving the voltage ratio of the transformer, the capacitance of the charging capacitor and the inductance of the coil as well as the resistance thereof (fixed parameters) out of consideration, the amplitude is dependent on two variable parameters. One variable parameter is the patient resistance to be identified and the other variable parameter is the energy that is regularly adjustable and stored in the charging capacitor. For identifying the patient resistance, thus, it is necessary to define the energy stored in the charging capacitor and to simultaneously take the amplitude of the secondary voltage into consideration in the evaluation of the measured quantity. This is complicated and, above all else, leads to more pronounced measuring tolerances.

SUMMARY OF THE INVENTION

It is object of the present invention to provide a method and apparatus of the type described above with which at least one variable parameter in the RLC discharge circuit can be identified independently of the magnitude of the amplitude of the output electrical pulse.

The above object is achieved in a method and apparatus wherein the chronological duration between two values of the electrical pulse at different times is measured using a timer circuit which is coupled to the RLC discharge circuit. The chronological spacing is evaluated and the result of the evaluation is used to define a parameter of the RLC discharge circuit.

A significant advantage of the invention is that one variable parameter in the RLC discharge circuit, for example, the patient resistance, can be identified completely independently of the magnitude of the amplitude of the output electrical pulse. This is achieved by measuring and evaluating the chronological spacing between two measurable (characteristic) values of the output electrical pulse. One characteristic value of the pulse, for example, can be the time at which the maximum value of the amplitude is reached. The invention, consequently, proceeds on the perception that the time at which a defined, measurable value of the amplitude of the output pulse occurs is reached entirely independently of the amount of the amplitude. Whereas, by contrast, the amount of the amplitude of the output pulse is dependent both on the energy stored in the charging capacitor as well as on the patient resistance, the chronological duration that is inventively selected for defining a variable parameter is completely independent of the energy stored in the charging capacitor. The fixed parameters in the RLC discharge circuit, namely the capacitance of the storage capacitor, the inductance of the coil and the internal ohmic resistance thereof, are known and are not made to be variable. Therefore, it is particularly the resistance of the biological tissue (patient resistance) that, in an embodiment of the invention, can be defined with high precision in a measuring means from these fixed, known parameters and from the measured, variable chronological duration. According to another version of the invention, a value table, for example, can be stored in the measuring means, a defined value of resistance of the biological tissue being allocated therein to a respective measurable chronological duration.

DESCRIPTION OF THE PREFERRED EMBODIMENTS

Figure 1:
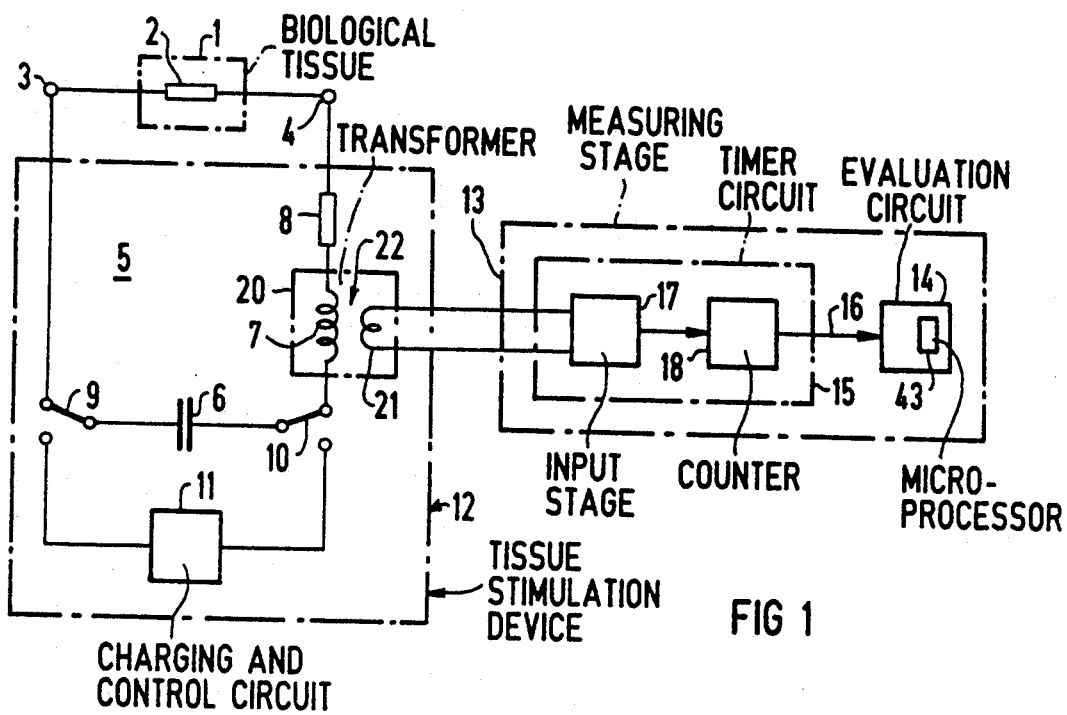
FIG. 1 is a basic diagram of an apparatus constructed in accordance with the principles of the present invention.

FIG. 1 shows an apparatus with which at least one parameter can be defined during the output of an electrical pulse to biological tissue 1. The biological tissue 1, for example, of a patient, has an ohmic resistance 2 that can vary dependent on the tissue 1 of the patient. The biological tissue 1 is connected via electrodes 3 and 4 to an RLC discharge circuit 5 formed by a storage capacitor 6 and a coil 7. A resistor 8 is also shown in the RLC discharge circuit 5, symbolizing the internal resistance of the coil 7. The storage capacitor 6 is connectable to a charging and control circuit 11 for charging via switches 9 and 10, which may be electronically fashioned and controlled. The charging and control circuit 11 swerves the purpose of charging the storage capacitor 6 and of controlling the switches 9 and 10, as a result of which the output of an electrical pulse from the RLC discharge circuit 5 to the biological tissue 1 can also be controlled. The RLC discharge circuit 5 and the charging and control circuit 11 is fashioned as a stimulation device 12 that can be employed in a current stimulation system, particularly in a defibrillator. The defibrillator 10 can also be implanted into the patient and can be connected via the electrodes (terminals) 3 and 4 to the biological tissue of the heart muscle.

A measuring stage 13 including an evaluation circuit 14 is coupled to the RLC discharge circuit 5. The measuring stage 13 includes a timer circuit 15. The timer circuit 15 is fashioned such that the chronological spacing between two characteristic values of the electrical pulse that can be supplied to the biological tissue 1 can be measured and can be output to the evaluation circuit 14 of the measuring means 13 as an electrical signal via the line 16. A parameter in the RLC discharge circuit 5, particularly the value of the resistance 2 of the biological tissue 1, is calculated, for example, with the assistance of a microprocessor 43, in the evaluation circuit 14 from the timing signal received via the line 16.

The timer circuit 15 can contain a plurality of components. An input stage 17 serves the purpose of recognizing characteristic (measurable) values of the electrical pulse that can be output to the biological tissue 1. Dependent on such recognized, characteristic values, the input stage 17 can then control a counter circuit 18 that, for example, counts clock pulses. Given the presence of a first characteristic value, thus, the counting circuit 18 can be started with a signal from the input stage 17 and can be stopped given the presence of a second characteristic value. The number of counted pulses represents a measure for the chronological spacing (chronological duration) between the two characteristics values and is supplied to the evaluation circuit 14 as an electrical signal via the line 16. Such a timer circuit 15 can be manufactured with little outlay and with high measuring precision (low measuring tolerance).

Figure 2:
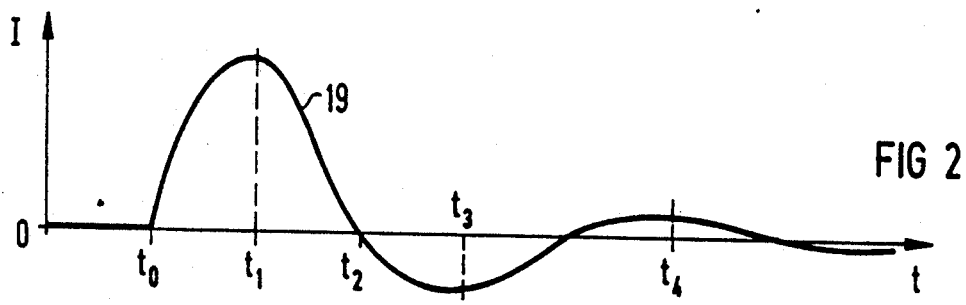
FIG. 2 shows an an periodically attenuated oscillation that can be supplied as an output to biological tissue as an electrical pulse by the apparatus of FIG. 1.

FIG. 2 shows a typical electrical pulse 19 that can be output to the biological tissue 1 as a current circuit curve. The electrical pulse 19 has the characteristic of an attenuated oscillation. Other pulse shapes, for example an aperiodically attenuated oscillation, can also occur dependent on the electrical parameters in the RLC discharge circuit 5 of FIG. 1. As characteristic values that are simple to identify, the electrical pulse 19 has, for example, the pulse start at time $t_0$, a maximum value of the amplitude at time $t_1$ and a zero-axis crossing at time $t_2$, as well as low maximum values at the times $t_3$ and $t_4$. Consequently, the input stage 17 in FIG. 1 can be fashioned such that it recognizes, for example, the pulse start $t_0$ and/or the maximum value of the amplitude at time $t_1$ and/or the zero-axis crossing of the amplitude at time $t_2$. All times $t_1$ through $t_4$ are dependent on the capacitance of the storage capacitor 6, on the inductance of the coil 7, on the internal resistance 8 of the coil 7 (fixed parameters) and on the changing value of the resistance 2 of the biological tissue 1 (variable parameter).

In order to calibrate the apparatus of FIG. 1, the manufacturer can first arrange high-precision resistors between the electrodes 3 and 4 and the times between two characteristic values, for example, between $t_0$ and $t_1$, measured in the evaluation circuit 14 upon the output of a pulse can be stored, in one version of the invention, in the microprocessor 43 as value table in relation to the value of the precision resistor. intermediate values can be calculated by interpolation. According to another version of the invention, however, it is also possible to calculate the chronological duration until a characteristic value of the pulse 19 is reached dependent on the changing value of the resistance 2 and on the fixed values of the coil 7 (plus the resistance 8 thereof) and the of the RLC discharge circuit are known, for example, from the periodical "International Medical Device and Diagnostic Industry", May/June 1990, page 48.

In a further embodiment of the invention, the measuring stage 13 shown in FIG. 1 can be coupled to the RLC discharge circuit 5 via a stage 20 that differentiates the electrical pulse 19. For example, a capacitive coupling via a capacitor (not shown) can be provided for that purpose. It is especially advantageous when the timer circuit 15 has its input side connected to the secondary winding 21 of a transformer 22, which forms the stage 20 that differentiates the electrical pulse 19.

In order to keep the number and size of the component parts that influence the measuring precision low, the coil 7 in the RLC discharge circuit 5 is fashioned as primary winding of the transformer 22. For further improvement of the measuring precision, the transformer 22, preferably a transformer that can be operated in a no-load condition, is high-impedance coupled to the timer circuit 15. As a result, it is also possible to fashion the secondary winding 21 with only a few turns, so that a precise, measurable no-load voltage arises at the secondary winding, even when the transformer 22 is an air-core transformer, as shown.

Figure 3:
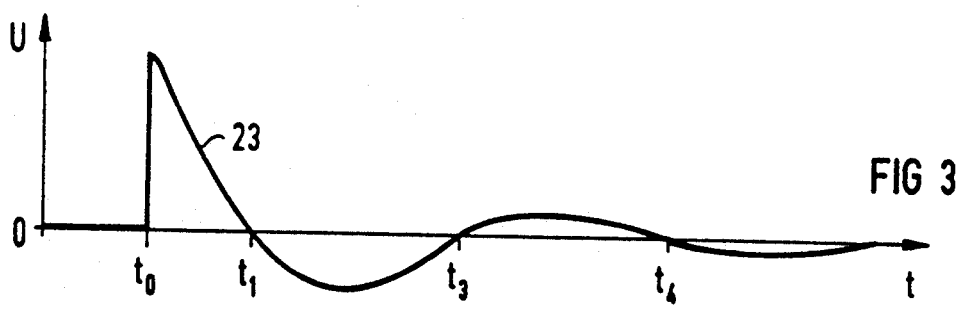
FIG. 3 is a differentiated signal derived from the electrical pulse of FIG. 2.

The no-load voltage of the secondary winding 21 of the air-core transformer 22 is shown in FIG. 3. This no-load voltage forms a differential signal 23 that is derived from the electrical pulse 19. Mathematically considered, this differentiated signal 23 consequently corresponds to the first derivative of the curve of the electrical pulse 19. The chronological coincidence of the first positive peak of the curve 19 at time $t_1$ with a first zero-axis crossing of the curve 23 is shown in FIGS. 2 and 3. Consequently, the negative peak of the curve 19 at the time $t_3$ corresponds to a zero-axis crossing of the curve 23 at the same time. The derivative of a differentiated signal from the electrical pulse 19 has the significant advantage that the time $t_1$, which corresponds to the time at which the first maximum value of the amplitude of the pulse 19 is reached, can be defined with utmost precision by the chronologically corresponding zero-axis crossing in curve 23. It is also advantageous that the time $t_1$ established by the first maximum value can also be unambiguously acquired even given aperiodically attenuated shapes of the pulse 19.

Figure 4:
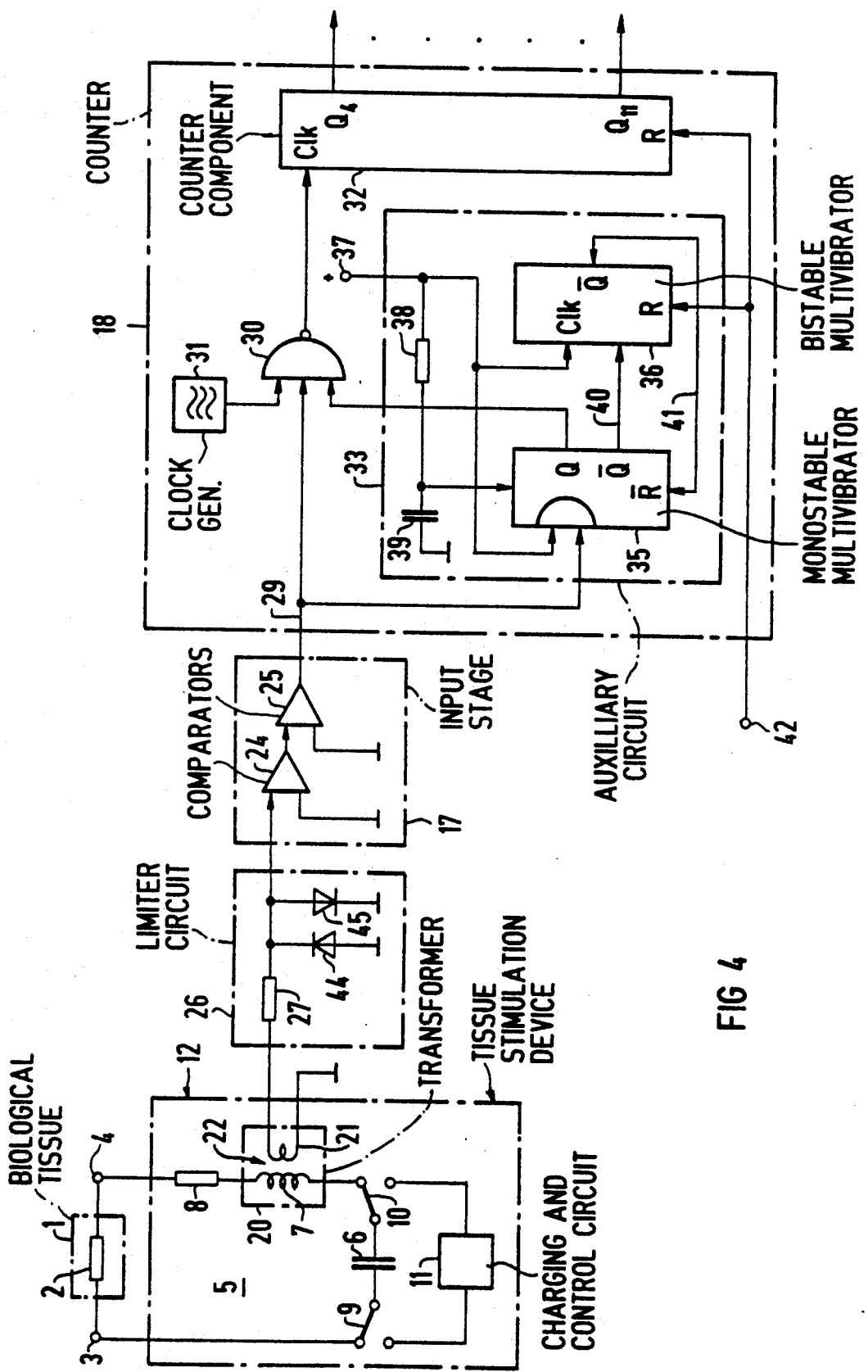
FIG. 4 is a partial circuit diagram of the apparatus of FIG. 1 showing a more detailed illustration of a timer circuit.

The counting circuit 18 and the input stage 17 of the timer circuit 15 shown generally in FIG. 1 are shown in FIG. 4 as a specific embodiment. The input stage 17 contains two comparator circuits 24 and 25 that are connected via a limiter circuit 26 to the RLC discharge circuit 5 in the stimulation device 12 of the apparatus of the invention. The limiter circuit 26 contains a limiting resistor 27 and two diodes 44 and 45 connected with opposite polarity. The voltage peak of the differentiated signal 23 that follows the time $t_0$ in FIG. 3 is limited with the limiter circuit 26 (which is not absolutely required) in order to protect the input of the following comparator circuit 24 from overvoltages. The output of the comparator 24 is connected to an input of the comparator 25, as a result of which each zero-axis crossing of the differentiated signal of curve 23 in FIG. 3 can be identified with particular precision.

Figure 5:
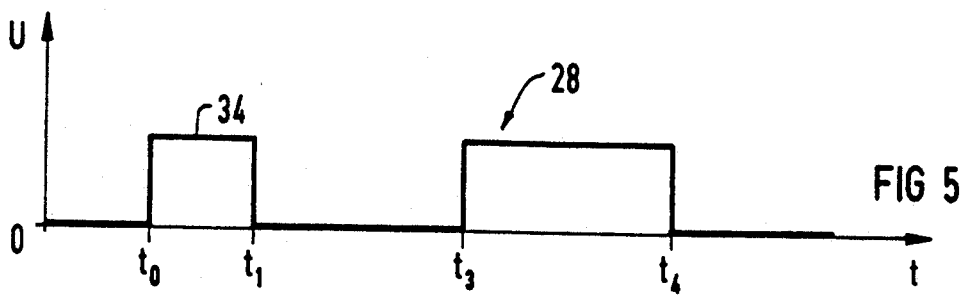
FIG. 5 shows a square-wave signal generated within the timer circuit of FIG. 4.

As a result of the specific fashioning of the input stage 17 of FIG. 4, a square-wave signal 28, shown in FIG. 5, arises at the output thereof. A gate circuit 30 in the counting circuit 18 is driven via a line 29 with this square-wave signal 28 (FIG. 4). The gate circuit 30 receives clock pulses from a clock generator 31 via another input. The clock pulses are counted in a counter component 32 for the time during which the gate circuit 30 has been opened, for example due to the square-wave signal 28 (pulse 34) on the line 29. For example, an 11-bit counter IC having the type designation 4020 is suitable as counter component 32, this integrated circuit 4020 having parallel outputs Q4 through Q11. The electrical output signal from the counter component 32 can then be supplied via a correspondingly multi-poled line 16 to the evaluation circuit 14 for the calculation of a parameter, as already set forth with reference to FIG. 1.

If the electrical pulse supplied as an output to the biological tissue 1 can have the shape of an attenuated oscillation according to curve 19 in FIG. 2, it is expedient to provide an auxiliary circuit 33 of FIG. 4 in a further embodiment of the invention. With this auxiliary circuit 33, the gate circuit 30 is additionally controlled such that counting pulses from the clock generator 31 of FIG. 4 can only proceed to the counter component 32 during the chronological duration of a first pulse 34 ($t_0$ through $t_1$) of the square-wave signal 28 of FIG. 5. To that end, the auxiliary circuit 33 includes two trigger circuits, one trigger circuit being a monostable multivibrator 35 and the other trigger circuit being a bistable multivibrator 36. The monostable multivibrator 35 receives a positive operating voltage via the terminal 37, this positive operating voltage also supplying a RC timer element formed by a resistor 38 and a capacitor 39. The monostable multivibrator 35 is started at time $t_0$ by the leading edge of the pulse 34 of the square-wave signal 28 that arises on the line 29 given the output of a pulse 19 to the biological tissue 1. As a result, an output signal with which the gate circuit 30 is opened during the hold time of the multivibrator 35 (which is adjustable with the RC element 38 and 39) is generated at an output Q of the multivibrator 35. An inverting output Q is connected via a line 40 to a control input CLK of the bistable multivibrator 36. The bistable multivibrator 36 then inhibits the monostable multivibrator 35 via a line 41, so that the latter can no longer be triggered by any pulses of the square-wave signal 28 which may follow. Before the output of another electrical pulse 19 to the biological tissue 1, the auxiliary circuit 33 and the counter 32 can be reset to their initial condition by a reset signal, for example from the charging and control circuit 11, that can be supplied via the terminal 42. For example, a module having the type designation 4538 can be employed as the monostable multivibrator 35 and a module having the type designation 4013 can be employed as the bistable multivibrator.

For each electrical pulse 19 that can be supplied as an output to the biological tissue 1, the pulse start at time $t_0$ and the time $t_1$ of the maximum of the pulse amplitude represent values for such a pulse that are especially characteristic and precisely measurable. The chronological duration between the time $t_0$ and the time $t_1$, consequently, can be measured with high precision according to the present invention and is not dependent on the energy stored in the storage capacitor 6. A further parameter in the RLC discharge circuit 5, such as the output energy to the biological tissue 1, can likewise be defined with high precision. To that end, the output energy output to the biological tissue 1 is calculated from the precisely measured value of the resistance 2 of the biological tissue 1 as well as the coil resistance 8 and from the energy stored in the storage capacitor 6, according to the equation:

$$W2 = W1 \times R2/(R2+R8)$$

wherein
W2 = the output energy to the biological tissue 1,
W1 = the energy stored in the storage capacitor 6,
R2 = the resistance 1 of the biological tissue 2, and
R8 = the coil resistance 8.

This calculation of a further parameter is possible without particular outlay, for example with the microprocessor 43 allocated to the evaluation circuit 14. Since the value of the resistance 2 of the biological tissue 2 (R2) was inventively calculated independently of the energy W1 stored in the storage capacitor 6, the output energy W2 to the biological tissue 1 can therefore already be defined with high precision.

Although further modifications and changes may be suggested by those skilled in the art, it is the intention of the inventors to embody within the patent warranted hereon all changes and modifications as reasonably and properly come within the scope of their contribution to the art.

I claim as my invention:

1. A method for defining at least one parameter in an RLC discharge circuit which supplies an electrical pulse signal as an output to biological tissue, said method comprising the steps of:
    measuring the chronological spacing between two measurable values of said electrical pulse signal;
    using a value of said electrical pulse signal at a start of said electrical pulse signal as a chronologically first one of said two measurable values; and evaluating said chronological spacing and defining a parameter of said RLC discharge circuit based on said chronological spacing.

2. A method as claimed in claim 1 comprising the additional step of:
    using a zero-axis crossing of said electrical pulse signal as a chronologically second one of said two measurable values.

3. A method as claimed in claim 1 comprising the additional step of taking a first derivative of a signal curve of said electrical pulse signal, and wherein the step of measuring a chronological spacing is further defined by measuring a chronological spacing between two measurable values of said first derivative.

4. A method as claimed in claim 3 comprising the additional step of:
    using a start of said first derivative as a chronologically first of said two measurable values.

5. A method as claimed in claim 4 comprising the additional step of:
    using a zero-axis crossing of said first derivative as a chronologically second of said two measurable values.

6. A method as claimed in claim 1 wherein a signal corresponding to said electrical pulse signal has a first maximum amplitude value, and comprising the additional steps of:

obtaining a first derivative of said signal corresponding to said electrical pulse signal, said first derivative having a first zero-axis crossing corresponding to said first maximum amplitude value; and using said first zero-axis crossing as one of said two measurable values.

7. A method as claimed in claim 1 wherein said RLC discharge circuit has a plurality of fixed, known parameters, and comprising the additional step of:

identifying a parameter of said biological tissue from said fixed-known parameters of said RLC discharge circuit.

8. A method as claimed in claim 7 wherein said parameter of the biological tissue is the resistance of the biological tissue.

9. A method as claimed in claim 8 wherein said fixed, known parameters of said RLC discharge circuit include the capacitance of and the energy stored in a storage capacitor in said RLC discharge circuit, the inductance of a coil in said RLC discharge circuit, and the internal ohmic resistance of said coil, and comprising the additional steps of:

adding said identified parameter of resistance of the biological tissue and said coil resistance to obtain a sum:

dividing the identified parameter of the resistance of said biological tissue by said sum of said identified parameter of resistance of the biological tissue and said coil resistance to obtain a quotient; and defining the output energy to said biological tissue by multiplying said quotient by said energy stored in said storage capacitor.

10. In an apparatus for supplying an electrical pulse signal to biological tissue as an output of an RLC discharge circuit, the improvement comprising:

timer means for measuring a chronological duration between two measurable values of said electrical pulse signal, a chronologically first of said two measurable values being a value of said electrical pulse signal at a start of said electrical pulse signal; and means for evaluating said chronological duration and for defining a parameter of said RLC discharge circuit based on said chronological duration.

11. The improvement of claim 10 further comprising means for differentiating said electrical pulse signal to obtain a first derivative signal for use by said timer means as a measurement of said chronological duration.

12. The improvement of claim 11 wherein said means for differentiating is a transformer coupling said timer means to said RLC discharge circuit.

13. The improvement of claim 12 wherein said transformer has a secondary winding across which said first derivative is present, said first derivative having a first zero-axis crossing, and wherein said timer means is a means for measuring the chronological duration between a start of said first derivative signal and said first zero-axis crossing.

14. The improvement of claim 13 wherein said timer means includes counter means for generating a count starting at said start of said first derivative signal and ending at said first zero-axis crossing, said count corresponding to said chronological duration.

15. The improvement of claim 12 wherein said RLC discharge circuit is a primary winding of said transformer.

16. The improvement of claim 15 wherein said means for evaluating is a microprocessor having a value table in which a plurality of zero-axis crossings of said first derivative signal are stored, each zero-axis crossing corresponding in said value table to a different resistance value of said biological tissue.

17. The improvement of claim 15 wherein said transformer has a secondary winding, across which said first derivative signal is present, said first derivative signal having a zero-axis crossing, and wherein said timer means is a means is a means for measuring the chronological duration between a start of said first derivative signal and said zero-axis crossing.

18. The improvement of claim 17 wherein aid timer means includes comparator means, having an input connected to said secondary winding for identifying said zero-axis crossing.

19. The improvement of claim 17 wherein said timer means includes counter means for generating a count starting at said start of said first derivative signal and ending at said zero-axis crossing, said count corresponding to said chronological duration.

20. The improvement of claim 17 wherein said transformer is a transformer operable in a no-load condition, and is high-impedance coupled to said timer means.

21. The improvement of claim 20 wherein said transformer is an air core transformer.

22. The improvement of claim 20 wherein said secondary and primary windings of said transformer have respective numbers of turns, and wherein said number of turns in said secondary winding is small compared to said number of turns in said primary winding.

23. The improvement of claim 20 wherein said secondary winding of said transformer has a no-load voltage thereacross forming said first derivative signal.

24. The improvement of claim 11 wherein said means for differentiating is a transformer operable in no-load condition which is high-impedance coupled to said timer means.

25. The improvement of claim 24 wherein said transformer is an air core transformer.

26. The improvement of claim 24 wherein said transformer has a primary winding, and wherein said primary winding and said secondary winding have respective number of turns, said number of turns in said secondary winding being small compared to said number of turns in said primary winding.

27. The improvement of claim 16 wherein said RLC discharge circuit includes a coil having a coil resistance and a storage capacitor having energy stored therein, and wherein said microprocessor includes means for dividing a selected value of resistance of biological tissue from said value table by the sum of said selected value of resistance and said coil resistance to obtain a quotient, and means for defining output energy to said biological tissue by multiplying said quotient by said energy stored in said storage capacitor.

* * * * *